United States Patent [19]
Lechot

[11] Patent Number: 6,106,536
[45] Date of Patent: Aug. 22, 2000

[54] SURGICAL REAMER

[75] Inventor: André Lechot, Orvin, Switzerland

[73] Assignee: Precifar SA, Orvin, Switzerland

[21] Appl. No.: 09/274,950

[22] Filed: Mar. 23, 1999

[30] Foreign Application Priority Data

Apr. 2, 1998 [CH] Switzerland ............................. 793/98

[51] Int. Cl.[7] ................................................. A61B 17/00
[52] U.S. Cl. ......................................................... 606/180
[58] Field of Search ................................. 606/80, 81, 83, 606/84, 170, 171, 180

[56] References Cited

U.S. PATENT DOCUMENTS

| | | |
|---|---|---|
| 4,023,572 | 5/1977 | Weigand et al. . |
| 5,348,023 | 9/1994 | McLucas .................................. 606/170 |
| 5,658,290 | 8/1997 | Precifar . |
| 5,913,858 | 6/1999 | Calandruccio et al. ................... 606/80 |

FOREIGN PATENT DOCUMENTS

| | | |
|---|---|---|
| 0 782 840 A1 | 7/1997 | European Pat. Off. . |
| 2 281 095 | 3/1976 | France . |

*Primary Examiner*—Michael Buiz
*Assistant Examiner*—Vy Q. Bui
*Attorney, Agent, or Firm*—Bugnion S.A.; John Moetteli

[57] ABSTRACT

A surgical reamer, intended in particular for the shaping of the cotyloid cavity in the event of a replacement of a hip joint by total prosthesis. It is in the form of a hollow body of rotation equipped with fixing means (3, 4) for attachment to a reamer spindle in order to be driven in rotation. The hollow body (1) is supported by a bar (2) whose axis coincides at least approximately with the axis of rotation of the reamer and it extends essentially on one side of a plane containing the axis of the bar (2), at least part of the length of the rim of the hollow body forming a cutting edge (5). Such a reamer makes it possible to shape accurately a cavity of hemispherical or other shape, according to the shape of the hollow body.

9 Claims, 2 Drawing Sheets

U.S. Patent Aug. 22, 2000 Sheet 1 of 2 6,106,536
Fig.1
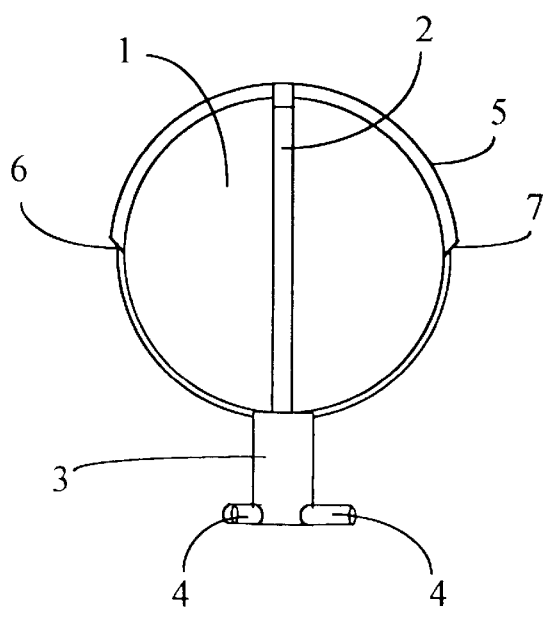
Fig.2
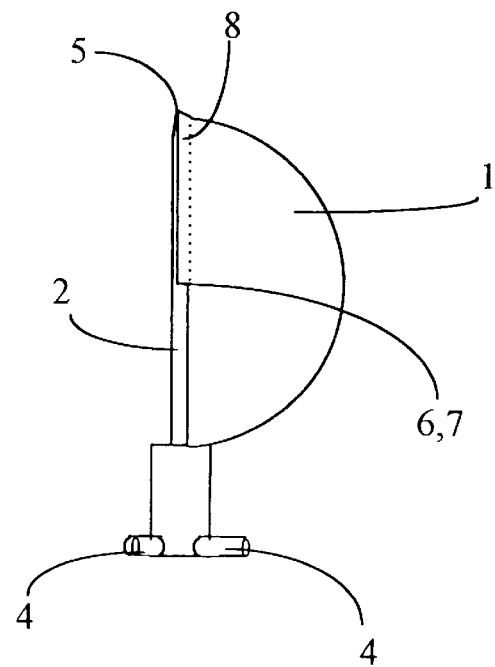
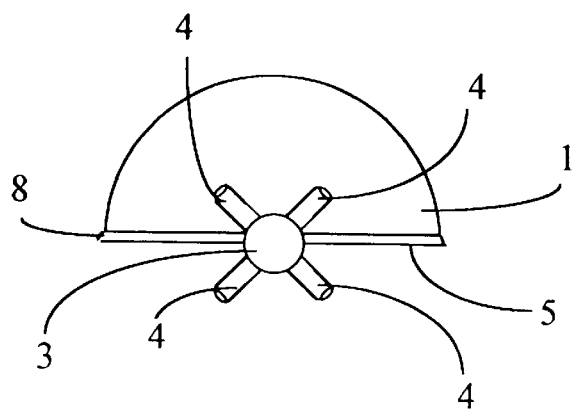
Fig.3

SURGICAL REAMER

BACKGROUND OF THE INVENTION

The present invention relates to a surgical reamer, intended in particular for the shaping of the cotyloid cavity in the event of a replacement of the hip joint by total prosthesis, in the form of a hollow body cut out from a body of rotation equipped with fixing means for attachment to a reamer spindle in order to be driven in rotation.

Patent FR 2 281 095, the content of which is incorporated by reference, has disclosed a surgical reamer in the form of a hemispherical cap equipped with a diametral bar for its attachment to a reamer spindle in order for it to be driven in rotation about an axis coinciding with the axis of symmetry of the hemispherical cap. The surface of the cap is provided with numerous cutting teeth performed by perforating the metal of the cap and pushing it outwards. This design, reminiscent of a cheese grater, has been adopted in subsequent embodiments, such as the embodiments described in U.S. Pat. No. 5,658,290 and patent application EP 0,782,840, the contents of which are incorporated by reference.

Such reamers ensure effective reaming, but do not make it possible to obtain a high precision cavity. However, the current trend in the fitting of prostheses is to discontinue the use of adhesive or screws. It would consequently be desirable to be able to shape the cotyloid cavity much more precisely and more smoothly than can be done by means of the known reamers.

SUMMARY OF THE INVENTION

The object of the present invention is to provide a surgical reamer making it possible to shape accurately a cavity of hemispherical or other shape.

The reamer according to the invention is a reamer wherein the hollow body is supported by a bar whose axis coincides at least approximately with the axis of rotation of the reamer, the hollow body extends essentially on one side of a plane containing the axis of said bar, and at least part of the length of its rim forms a cutting edge.

According to a particular embodiment, the hollow body is in the form of a hemispherical cap. Such a reamer is particularly intended for the shaping of the cotyloid cavity of the hip.

A spherical surface could however also be reamed by a cap in the form of a sector of a sphere.

The hemispherical cap will generally be aligned in a manner such as to rotate about a diameter, but in some cases the cap may be slightly inclined relative to the axis of rotation, so that said axis of rotation is no longer in the meridian plane limiting the hemispherical cap.

The rim of the hollow body could possess a cutting edge over a length greater than half of its length, in particular, in the case of a hemispherical cap, over a length greater than half the circumference of its rim.

The outer surface of the reamer is, preferably, perfectly smooth and precision ground, enabling a smooth and accurate bone cavity to be shaped. For some applications, the surface of the reamer could however possess at least one cutting and support tooth analogous to the teeth of the prior art reamers and/or at least one support dome, so as to free a space behind the cutting edge, in order to avoid plugging.

According to one hemispherical cap embodiment, the rim of the cap possesses at least one offset situated in the equatorial plane of the sphere as reconstituted by the rotation of the cap. This offset makes it possible to monitor the penetration of the reamer into the bone cavity and to recognize the moment at which the depth of this cavity corresponds to the desired depth, which depth may vary depending on the implant.

BRIEF DESCRIPTION OF THE DRAWINGS

The attached drawings show, by way of example, two embodiments of the invention.

FIG. 1 is a view from the interior of a hemispherical reamer according to the first embodiment.

FIG. 2 is a profile view of the reamer shown in FIG. 1.

FIG. 3 is a view along the axis of rotation of this same reamer, showing the means for attaching it to a reamer spindle.

DETAILED DESCRIPTION OF THE PREFERRED OF THE EMBODIMENT(S)

Figure 4:
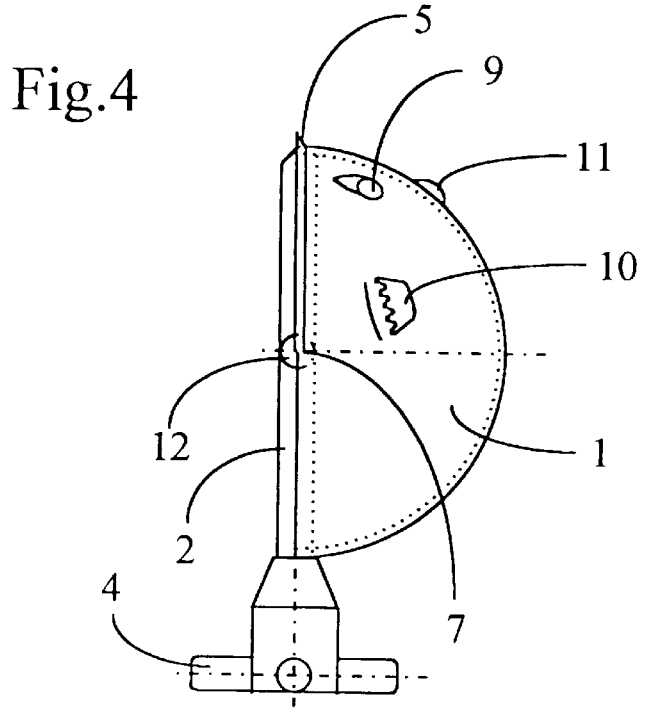
FIG. 4 shows an alternative embodiment of the reamer shown in FIGS. 1 to 3.

The reamer shown in FIGS. 1 to 3 essentially comprises a hollow hemispherical cap I made from steel, fitted with a diametral reinforcing bar 2 and rigidly attached to a cylindrical pin 3 equipped with four pegs 4, directed radially so as to form a cross for the attachment of the reamer to a reamer spindle as described in the applicant's U.S. Pat. No. 5,658,290, the content of which is incorporated by reference. The axis of the pin 3 determines the axis of rotation of the reamer which, in the embodiment shown, coincides with the axis of the small bar 2.

The outer surface of the cap 1 is smooth and may be precision ground. The rim of the cap 1 takes the form of a cutting edge 5 over half of the circumference of the rim opposite the means 3, 4 for attachment to the reamer spindle. The cutting edge 5 is thus situated in a plane containing the axis of rotation of the reamer. As with all reamers, a clearance 8 is necessary. This is obtained by slightly widening the rim of the cap over the ground portion.

The rim of the cap 1 additionally has two diametrally opposed offsets 6 and 7 situated at the ends of the cutting edge 5. The rim of the cap 1 is therefore not entirely in a single plane.

In operation, the reamer may be driven in either direction. During this rotation, either one of the halves of the edge 5 will be working. The offsets 6 and 7 make it possible to monitor the penetration of the reamer into the bone cavity. The offsets could therefore be replaced by any other reference mark allowing the same monitoring.

As has already been mentioned, the surface of the cap could possess one or more teeth as do the reamers of the prior art.

The means for attaching the reamer to the reamer spindle could, of course, be different and appropriate to the reamer spindle used.

The rim of the reamer could possess a single offset situated in the equatorial plane of the reconstituted sphere.

The hemispherical cap could be slightly inclined relative to the axis of rotation, with a view to shaping a slightly non-spherical cavity, in order to obtain a degree of tension on the prosthesis. In this case, the axis of rotation is no longer situated in the meridian plane limiting the cap, and the cutting edge 5 is situated in a plane slightly inclined relative to the axis of rotation.

The surface of the cap could possess cutting and support teeth. FIG. 4 shows examples of teeth. These teeth could have the shape of the tooth 9, that is to say a conventional shape obtained by cutting out the metal and pushing it outwards. These teeth 9 are distributed over the surface of the reamer and serve not only as cutting teeth but, primarily, as support teeth, ensuring a rearward clearance of the cutting edge 5, which clearance prevents plugging.

Said cutting and support teeth could likewise have the shape shown at 10, a special shape described in U.S. patent application Ser. No. 09/065,896, the content of which is incorporated by reference.

Instead of providing support teeth, it would be possible to provide support domes, such as the dome 11, that is to say a surface forming a type of bubble on the outer surface of the reamer. In the alternative embodiment shown in FIG. 4, the reamer further possesses a second reinforcement bar 12, more specifically two half-bars perpendicular to the main bar 2.

Figures 5, 6:
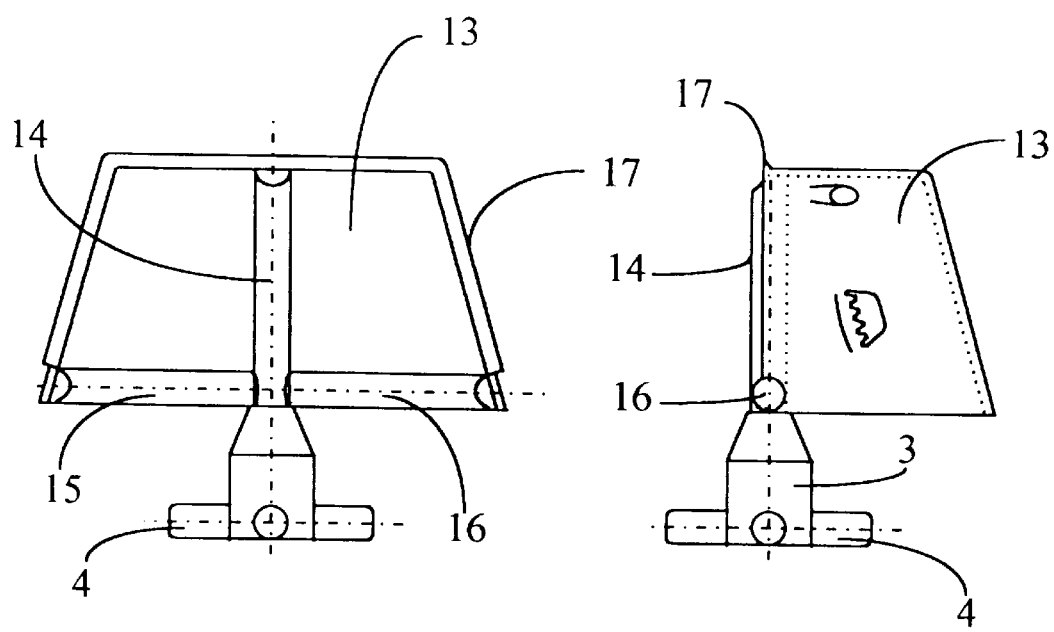
FIG. 5 is a view from the interior of a frustoconical reamer according to the second embodiment.
FIG. 6 is a profile view of this second embodiment.

FIGS. 5 and 6 show another embodiment of the reamer according to the invention. In this second embodiment, the hollow body is in the shape of a half-frustum 13 supported by an axial bar 4 coinciding with the axis of rotation of the reamer and two transverse bars 15 and 16 perpendicular to the bar 14. The rim of the hollow body 13 forms a cutting edge 17 similar to the edge 5 of the first embodiment. Like the hemispherical reamer, the frustoconical reamer can possess support teeth or support domes distributed over its surface. Such a frustoconical reamer will be used for the preparation of a bone cavity intended to receive an implant.

I claim:

1. A surgical reamer, intended in particular for the shaping of the cotyloid cavity in the event of a replacement of a hip joint by total prosthesis, in the form of a hollow body of rotation equipped with fixing means (3, 4) for attachment to a reamer spindle in order to be driven in rotation, wherein the hollow body (1; 13) is supported by a bar (2; 14) whose axis coincides at least approximately with the axis of rotation of the reamer, the hollow body extends essentially on one side of a plane containing the axis of said bar, and at least part of the length of its rim forms a cutting edge (5; 17) wherein the rim of the hollow body (1) possesses at least on reference mark (6,7) for monitoring the reamer penetration into the bone cavity.

2. The reamer as claimed in claim 1, wherein the hollow body is in the form of a cap (1) cut out from a sphere.

3. The reamer as claimed in claim 2, wherein the cap (1) is essentially hemispherical.

4. The reamer as claimed in claim 3, wherein the cutting edge (5) extends in a plane containing the axis of rotation of the reamer or in a plane parallel to said axis.

5. The reamer as claimed in claim 3, wherein the cutting edge (5) extends in a plane slightly inclined relative to the axis of rotation.

6. The reamer as claimed in claim 1, wherein the outer surface of the hollow body is entirely smooth.

7. The reamer as claimed in claim 1, wherein the outer surface of the hollow body possesses at least one cutting and support tooth (9; 10).

8. The reamer as claimed in claim 1, wherein the outer surface of the hollow body possesses at least one support dome (11).

9. The reamer as claimed in claim 1, wherein the hollow body is in the shape of a half-frustum (13).

* * * * *